United States Patent [19]

Forlot

[11] Patent Number: 4,939,167
[45] Date of Patent: Jul. 3, 1990

[54] USE OF 5-METHOXYPSORALEN AND OTHER FUROCOUMARINS AS JET LAG SUPPRESSANTS

[75] Inventor: Paul E. Forlot, Rungis, France

[73] Assignee: Jean Jacques Goupil, Boulange Billancourt, France

[21] Appl. No.: 225,902

[22] Filed: Jul. 29, 1988

Related U.S. Application Data

[63] Continuation-in-part of Ser. No. 223,191, Jul. 22, 1988, abandoned.

[51] Int. Cl.$^5$ .............................................. A61K 31/35
[52] U.S. Cl. .................................................... 514/455
[58] Field of Search ......................................... 514/455

[56] References Cited

U.S. PATENT DOCUMENTS 4,600,723  7/1986  Short et al. ......................... 514/416
4,699,781 10/1987  Ceoupil ............................... 514/873

OTHER PUBLICATIONS

Chemical Abstracts 107(15):130049m Souetre et al. 5-Methoxypsoralen Increases the Plasma Melatonin Levels in Humans, Soc. Invest. Dermat., 1987.

*Primary Examiner*—Douglas W. Robinson
*Assistant Examiner*—Raymond J. Henley, III
*Attorney, Agent, or Firm*—Darby & Darby

[57] ABSTRACT

Disclosed is use of 5-methoxypsoralen to prevent and suppress the symptons of jet lag.

11 Claims, No Drawings

USE OF 5-METHOXYPSORALEN AND OTHER FUROCOUMARINS AS JET LAG SUPPRESSANTS

This is a Continuation-in-Part of application Ser. No. 07/223,191 filed July 22, 1988 in the name of Paul FORLOT, entitled USE OF 5-METHOXYPSORALEN AS A JET LAG SUPPRESSANT now abandoned.

BACKGROUND OF THE INVENTION

1. Field of the Invention

The present invention relates to a method for suppressing or preventing symptoms of the human condition known as jet lag. Specifically, the invention is directed to a new use of 5-methoxypsoralen and related furocoumarin compounds.

2. Description of Prior Art and Other Published Information

Jet lag is a known psychological dislocation and disruption of bodily rhythms caused by high-speed travel across several time zones, usually in a jet airplane. In the course of such travel, the body's circadian clock is disturbed by the juxtaposition of night and day, or by merely a shift (usually of three hours or more) in the normal daily schedule to which the body is accustomed. Jet lag may cause a variety of maladies ranging from temporary exhaustion, insomnia, nausea and other, including gastrointestinal, ailments. Jet lag sufferers may experience a reduced desire and capacity to work or to pursue recreational activities and other normal functions usually associated with long-distance travel.

It is known that melatonin (N-acetyl-5-methoxytryptamine) is a sleep-inducing hormone secreted by the human pineal gland. Human melatonin secretion has a diurnal cycle with highest levels during the hours of darkness, typically peaking at about 11:00 p.m. (2300 hours), and reaching its lowest levels at about 7:00 a.m., or 0700 hours.

The linear furocoumarin, 5-methoxypsoralen, or 5-MOP, is well-known for its use in the treatment of various forms of psoriasis and other dermatoses such as vitiligo, atypical eczema and fungoid mycosis, and has been recognized as being especially useful in view of its efficacy and low toxicity. 5-MOP is also known for its beneficial effects in promoting "sun-tanning," or the browning of human skin as a result of the action of ultra-violet rays on the melanocytes of the skin, as described in Goupil, "Sun Products," U.S. Pat. No. 4,699,781.

Other furocoumarins have also been well-known for various uses, usually in the treatment of various skin conditions.

In a controlled study, 5-MOP (given orally in doses of 40 mg. to normal subjects at 2100 hours) increased the plasma level of melatonin from the second hour after administration. Increased secretion was greater after evening than after morning administration, as reported by Souetre, E. et al., "5-Methoxypsoralen Increases The Plasma Melatonin Levels In Humans," J. Invest. Derm., vol. 89:152-155 (1987).

Until the present invention, 5-MOP has not been known to constitute an effective preventive or suppressive medication for the symptoms of jet lag.

OBJECTS AND SUMMARY OF THE INVENTION

Accordingly, it is a broad object of the invention to provide an effective treatment for the suppression and prevention of the symptoms of jet lag.

It is an object of the invention to provide a new medication and method of use thereof which effectively reduces or eliminates the otherwise occurring psychological dislocation and disruption of bodily rhythms caused by high-speed travel across several time zones.

It is a further object to provide a preventive suppressant of jet lag symptoms which is easily administered, has low toxicity, and which is inexpensively synthesized and manufactured.

These and other objects and advantages of the invention will be readily understood in conjunction with the following detailed description of the invention and the preferred embodiments thereof.

DETAILED DESCRIPTION OF THE PREFERRED EMBODIMENTS

An effective treatment for suppressing the symptoms of jet lag has as its active ingredient 5-methoxypsoralen, which has the formula

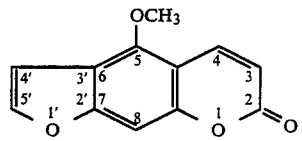

5-methoxypsoralen, or 5-MOP, as it is generally known, may be synthesized in a variety of ways. One such method of synthesis is disclosed in U.S. patent application Ser. No. 201,384, "5-Methoxy-Psoralen As New Medicament And Process For The Synthesis Thereof," filed May 31, 1988, that application and the present application having a common assignee, the disclosure of which is expressly incorporated herein by reference. In application Ser. No. 825,783, a method of synthesizing 5-MOP from phloroglucinol is described. This method is especially advantageous because the starting material is inexpensive, the synthesis is carried in relatively few steps, the process employs an inexpensive catalyst and produces a good yield.

Other methods of synthesizing 5-MOP are disclosed in Nikolaiski, "5-Oxy-Substituted Derivatives of Psoralene Useful In Dermatology," U.S. Pat. No. 4,217,445, the disclosure of which is hereby incorporated by reference.

5-MOP may be conveniently supplied in different forms, such as tablets, capsules, caplets and solutions. When supplied as tablets, suitable vehicles are employed having a base, for example, of lactose and Encompress. The tablets may be formulated using conventional procedures employing solid carriers and lubricants well-known in the art, for example as described in U.S. patent application Ser. No. 009,555, "5-Methoxy-Psoralen As New Medicament And Process For The Synthesis Thereof," filed Jan. 30, 1987, that application and the present application having a common assignee, the entire disclosure of which is expressly incorporated herein by reference.

When a person travels at high-speed (i.e, at a speed greater than the rate at which bodily rhythms adjust to a new time schedule) across several time zones, jet lag may be caused as in the following example, which is illustrative only. A subject travelling east from New York, USA to Zurich, Switzerland is transported across six time zones, so that the time of day and the subject's circadian clock are displaced in time by six hours. For example, when the time to retire to sleep arrives in Zurich at, say 11:00 p.m. (2300 hours), it is actually 5:00 p.m. (1700 hours EST) according to the subject's circadian rhythm and the natural diurnal variation in melatonin secretion. The subject is then an appropriate host for administration of a dose of 5-MOP sufficient to raise plasma melatonin levels to such level as will permit the subject to rest for an entire normal sleep period. When the subject awakes in Zurich the following morning, the body will have long since passed its peak melatonin level, as would normally be the case. Without having taken such a dose of 5-MOP, plasma melatonin levels would only recently have reached peak levels by awaking time in Zurich, and the sleep pattern would be disrupted.

The situation is seen to be even more pronounced when travelling westward. When the Zurich-based traveller retires to bed in New York at 11:00 p.m., it is already 5:00 a.m. (0500 hours) according the subject's circadian clock, and plasma melatonin levels are at or near the lowest levels of the diurnal cycle. It is thus difficult for the traveller to sleep at all. By midday the next day, the subject becomes increasingly uncomfortable and begins to suffer the aforementioned maladies associated with jet lag. In this case, administration of a jet lag suppressing dose of 5-MOP at bedtime (in New York) permits the subject to extend the sleep period by prolonging the elevated plasma melatonin level.

The preferred dosing method is to administer 5-MOP so as to cause registry of the thus-induced peak melatonin level at or near the normal time at which such melatonin level would be at peak if the traveller were accustomed to the local time zone. However, it is possible to vary the times and dosages of administration so that the induced melatonin level will be in registry with the normal melatonin level at some point post-administration. Determination of such dosages and timing may be easily made in accordance with clinical methods well-known to those of ordinary skill without undue experimentation.

5-MOP thus interacts with the body's hormonal system so as to effectively suppress or prevent the symptoms of jet lag. Because 5-MOP is believed to interfere with the hormonal balance, the required dosage of 5-MOP is not expected to be proportional to the host's body weight. Instead, once a minimum effective dosage is met or exceeded, the jet lag symptoms will be suppressed or prevented. Such a minimum effective dosage may be easily established according to well-known techniques and without resort to undue experimentation. Although 40 mg. doses have been found effective, of course, higher dosages of 5-MOP (which have been disclosed in the foregoing U.S. patent application Ser. No. 009,555 to be generally between 40 and 300 mg. per treatment per day) are also expected to be effective, albeit administration of such higher dosages would not be necessary.

Preferably, 5-MOP is administered one hour before the time that the subject should go to sleep, said time being determined as described above depending on the direction of travel and the time difference between the origin and destination.

The entire disclosure of all cited patents, patent applications and literature is incorporated by reference.

8-methoxypsoralen, a well-known isomer of 5-methoxypsoralen is also anticipated to be effective against jet lag at about the same dose levels as 5-MOP. Similarly, other furocoumarins such as

| | |
|---|---|
| $R_5 = R_8 = H$ | Psoralen |
| $R_5 = H; R_8 = -OCH_3$ | Xanthotoxin (=8-MOP) |
| $R_5 = H; R_8 = -O-CH_2-CH=C\begin{smallmatrix}CH_3\\CH_3\end{smallmatrix}$ | imperatorin |
| $R_5 = -OCH_3; R_8 = H$ | Bergapten (=5-MOP) |
| $R_5 = R_8 = -OCH_3$ | Isopimpinellin (5,8-DMOP) |
| 4,5',8-Trimethylpsoralen | (TMP = Trioxsalen) |

| | |
|---|---|
| $R_5 = R_6 = H$ | Angelicin |
| $R_5 = H; R_6 = -OCH_3$ | Sphondin |
| $R_5 = -OCH_3; R_6 = H$ | Isobergapten |
| $R_5 = R_6 = -OCH_3$ | Pimpinellin | are also anticipated to have the same effect. In particular, angelicin, and its derivatives (e.g., 4-methyl, 5-methyl, 5'-methyl, 4,5'-methyl, 5,5'-dimethyl) are also anticipated to be effective against jet lag in the manner described herein. All of these furocoumarins are either commercially available or can be synthesized by methods well-known in the art. Phototoxicity of several furocoumarins, while a drawback, is not expected to affect the present anti-jet lag use because the presently taught administration takes place at night in the absence of sunlight and is not a long-term treatment (unlike psoriasis and other skin conditions). Of course 5-MOP has substantially reduced phototoxicity compared to other furocoumarins. Angelicin and its derivatives are likewise not phototoxic.

It is also anticipated that all the foregoing compounds will be effective as nonnarcotic sleep inducers for longer term use against insomnia and related sleep disorders. For example, since 5-MOP is effective in inducing sleep when the jet-lagged subject would otherwise have difficulty in going to sleep, it is expected that 5-MOP via its activity in increasing the melatonin levels would be effective as a general use sleep-inducer, particularly when the sleep disorder is due to a hormonal or other chemical imbalance that prevents secretion of melatonin and the furocoumarin has the ability to cause such secretion. Decreased melatonin levels have been observed, for example, in aged subjects.

Dosages of the other furocoumarins of about 40 mg or more are expected to be effective for sleep inducement as indicated above for 5-MOP. The preferred time of administration is the same as that against jet lag. Phototoxic compounds are not preferred for long-term sleep inducement use.

I claim:

1. A method for suppressing the effects of jet lag in humans, comprising the step of administering to a host in need of such treatment, the host being accustomed to a first time zone and having travelled to a second time zone, a jet lag suppression effective amount of 5-methoxypsoralen.

2. The method of claim 1, comprising administering said 5-methoxypsoralen at a time such as to cause the plasma melatonin level of the host to be in registry with the melatonin level at the time in the second time zone at which said melatonin level would be in the host had the host been accustomed to the second time zone.

3. The method of claim 2, comprising administering said 5-methoxypsoralen at a time such as to cause the plasma melatonin level of the host to be at or near the peak melatonin level at the time in the second time zone at which said melatonin level would be at or near peak in the host had the host been accustomed to the second time zone.

4. The method of claim 1 wherein said amount is between about 40 and about 300 mg.

5. The method of claim 3 wherein said amount is between 40 and 300 mg.

6. A method for preventing the effects of jet lag in humans, comprising the step of administering to a host in need of such treatment, the host being accustomed to a first time zone and having travelled to a second time zone, a jet lag prevention effective amount of 5-methoxypsoralen.

7. The method of claim 6, comprising administering said 5-methoxypsoralen at a time such as to cause the plasma melatonin level of the host to be in registry with the melatonin level at the time in the second time zone at which said melatonin level would be in the host had the host been accustomed to the second time zone.

8. The method of claim 7, comprising administering said 5-methoxypsoralen at a time such as to cause the plasma melatonin level of the host to be at or near the peak melatonin level at the time in the second time zone at which said melatonin level would be at or near peak in the host had the host been accustomed to the second time zone.

9. The method of claim 6 wherein said amount is between 40 and 300 mg.

10. The method of claim 8 wherein said amount is between 40 and 300 mg.

11. A method for suppressing the effects of jet lag in humans, comprising the step of administering to a host in need of such treatment, the host being accustomed to a first time zone and having travelled to a second time zone, a jet lag suppression effective amount of a member selected from the group consisting of psoralen, xanthotoxin, imperatorin, bergapten, isopimpinellin, trioxsalen, angelicin, methylated derivatives of angelicin, sphondin, isobergapten and pimpinellin.

* * * * *